United States Patent [19]

Cammack et al.

[11] 4,302,186
[45] Nov. 24, 1981

[54] ORAL HYGIENE APPLIANCES

[75] Inventors: Michael A. Cammack; Christopher W. Elkins; Clarence J. Hickman; Keith M. Mullins, all of Ft. Collins, Colo.

[73] Assignee: Teledyne Industries, Inc., Ft. Collins, Colo.

[21] Appl. No.: 97,039

[22] Filed: Nov. 23, 1979

[51] Int. Cl.³ .......................................... A61C 17/02
[52] U.S. Cl. .................................... 433/80; 128/62 A
[58] Field of Search .................. 128/62 A, 66; 433/80

[56] References Cited

U.S. PATENT DOCUMENTS

| 3,771,517 | 11/1973 | Radecki | 128/66 |
| 3,771,557 | 11/1973 | Moret et al. | 128/66 |
| 3,871,560 | 3/1975 | Crippa | 128/62 A |
| 4,094,311 | 6/1978 | Hudson | 128/62 A |
| 4,109,650 | 8/1978 | Peclard | 128/66 |
| 4,141,352 | 2/1979 | Ebner et al. | 128/62 A |

Primary Examiner—Robert Peshock
Attorney, Agent, or Firm—Hugh H. Drake

[57] ABSTRACT

An oral hygiene appliance is of the kind which includes a supply of liquid, a pump and a hand-held tip for directing the liquid where desired. A housing defines a cavity which has a surrounding wall closed by opposing end walls, the pump being seated within the cavity. A reservoir is closed at one end and has a shape in conformity with the housing to telescope thereover in covering relationship. Defined in one end of the reservoir is a valve seat which cooperates with a valve that closes during removal of the reservoir from the housing. On that end of the reservoir also is a coupling element which cooperates with a coupling member disposed in the surrounding wall of the housing. When that coupling relationship is established, the reservoir is seated on top of a side surface of the housing which, in turn, is lying on a table or the like. An outlet in the housing communicates with the hand-held tip and the pump is connected between that outlet and the coupling member. Particular pump structure, electrical switching mechanism and other mounting and assembly features are described and illustrated.

30 Claims, 12 Drawing Figures

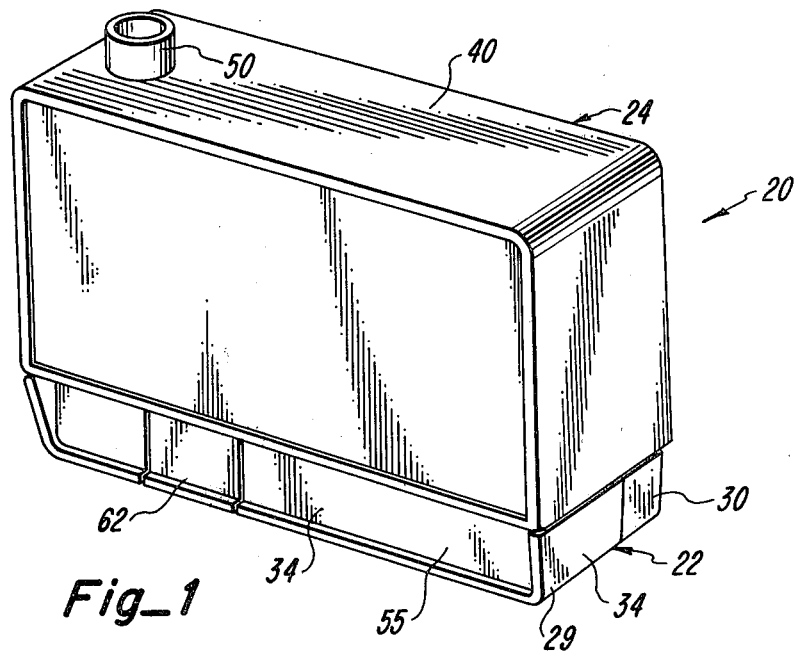
Fig_1
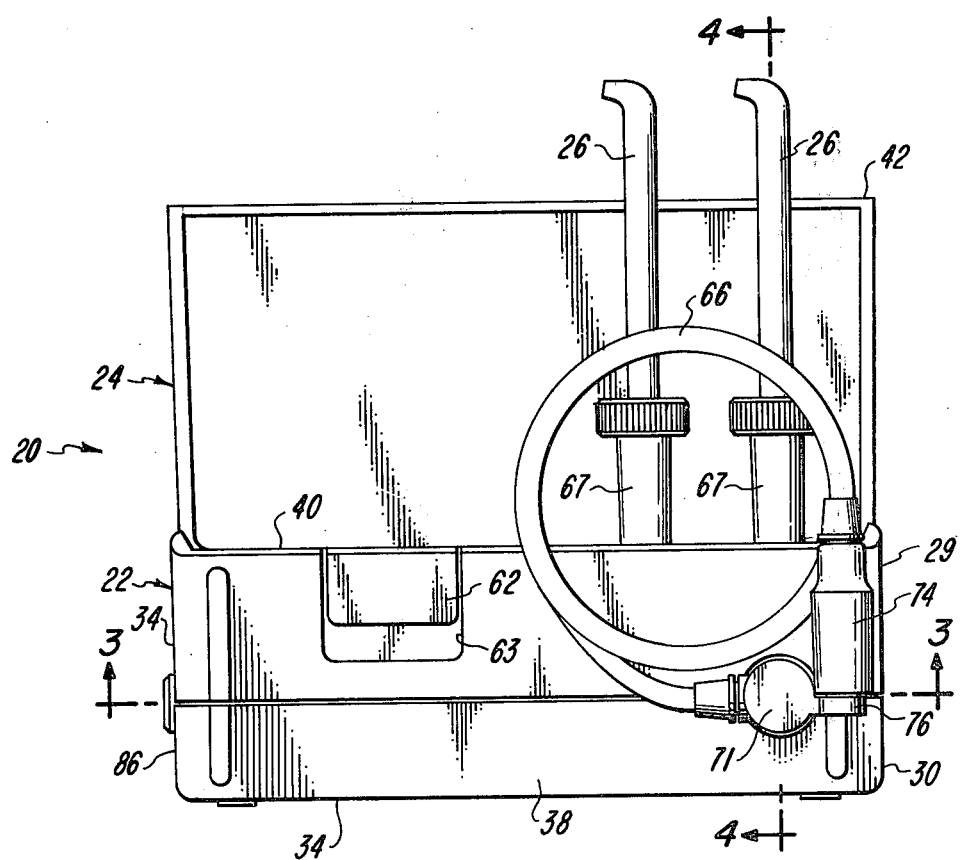
Fig_2

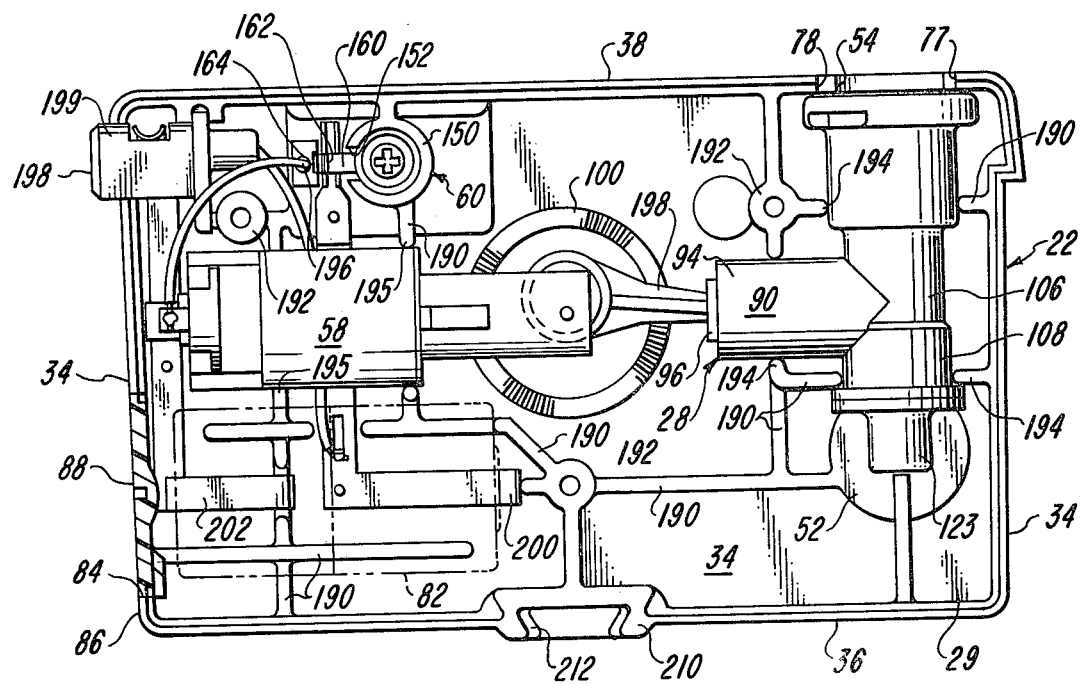
Fig_3
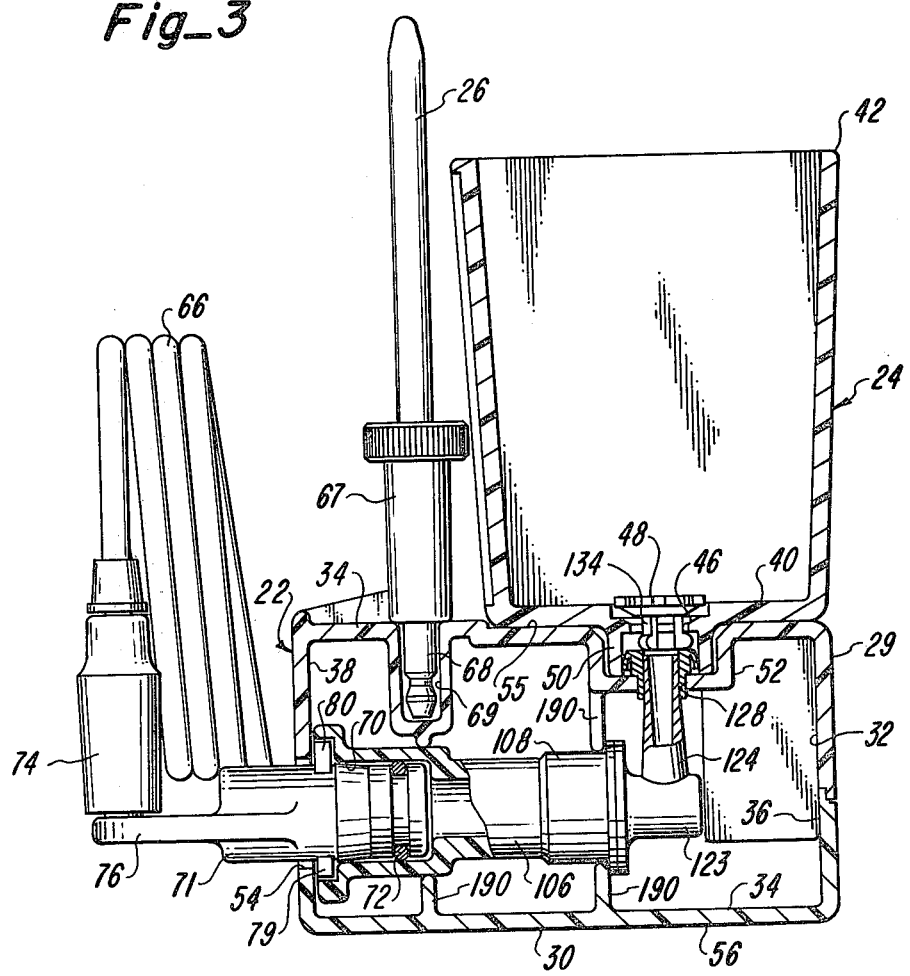
Fig_4

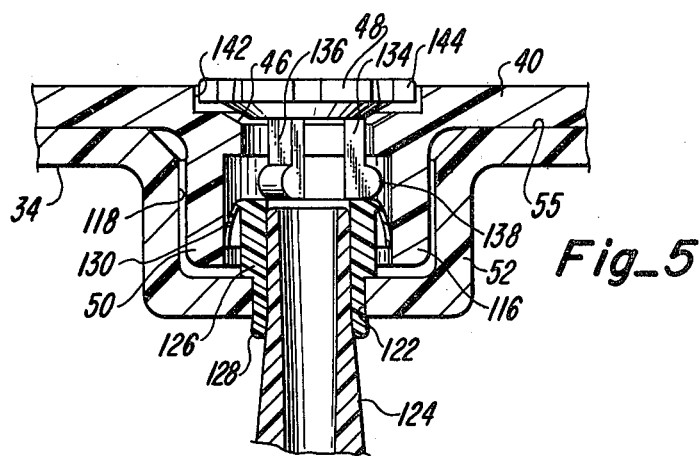
Fig_5
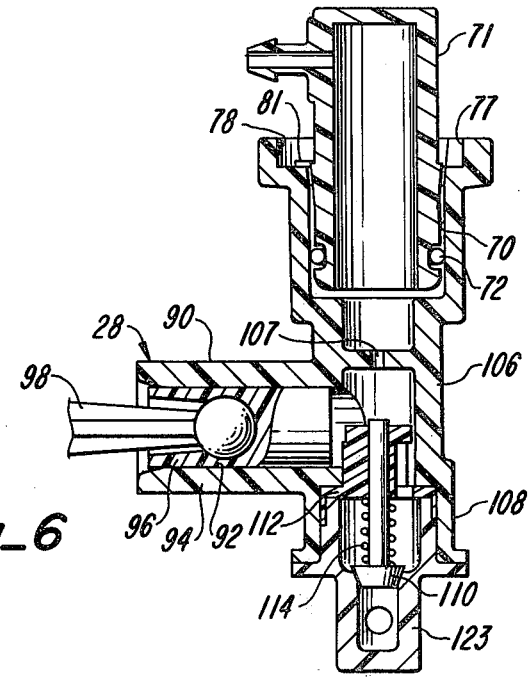
Fig_6
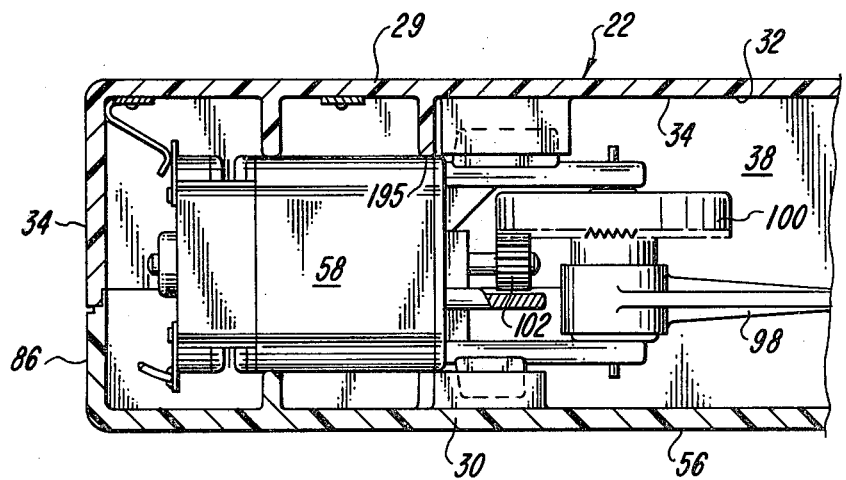
Fig_7

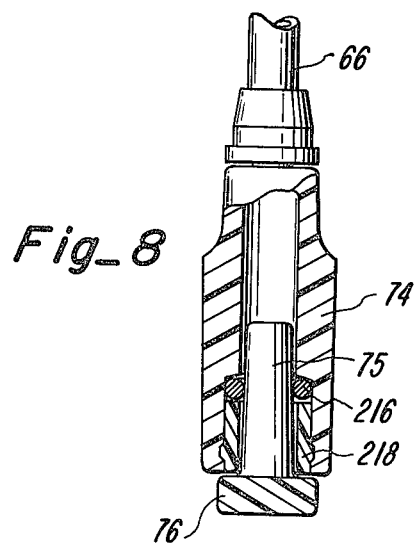
Fig_8
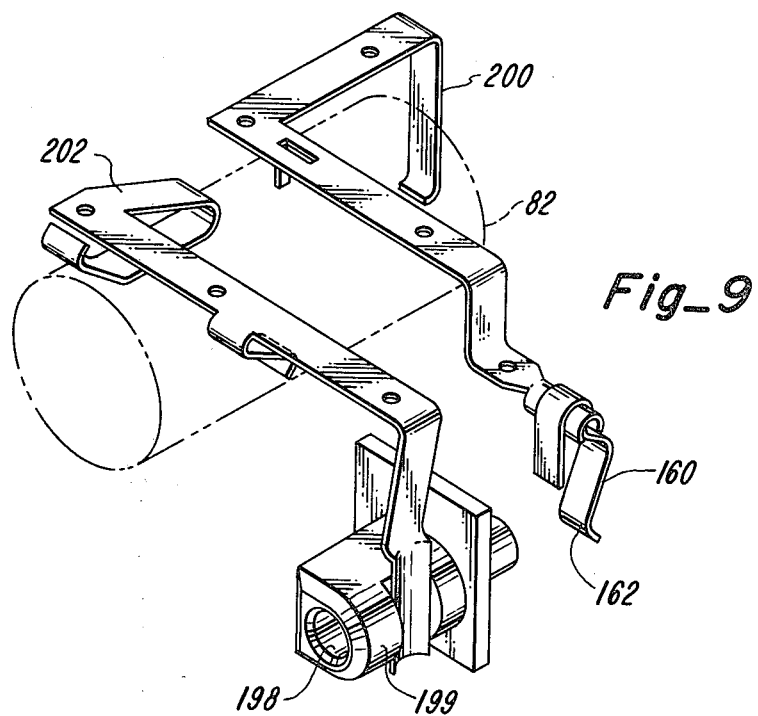
Fig_9

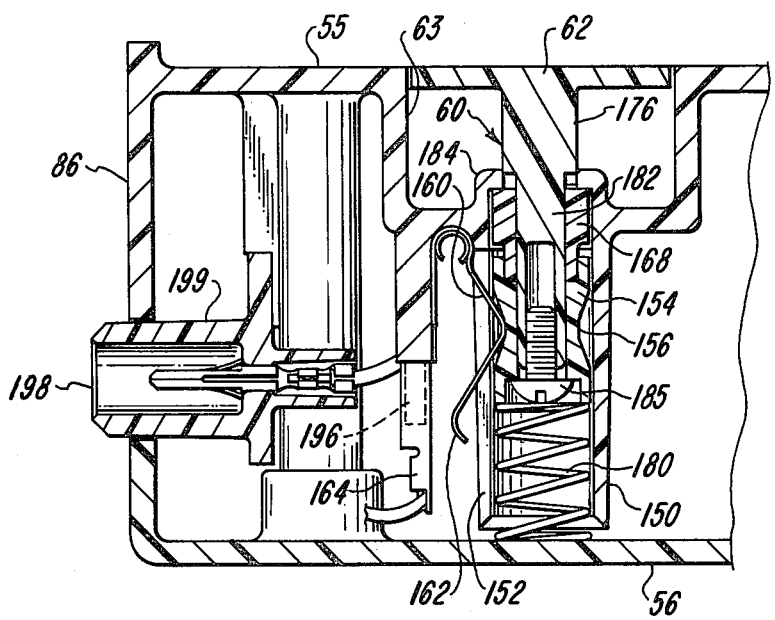
*Fig_11*
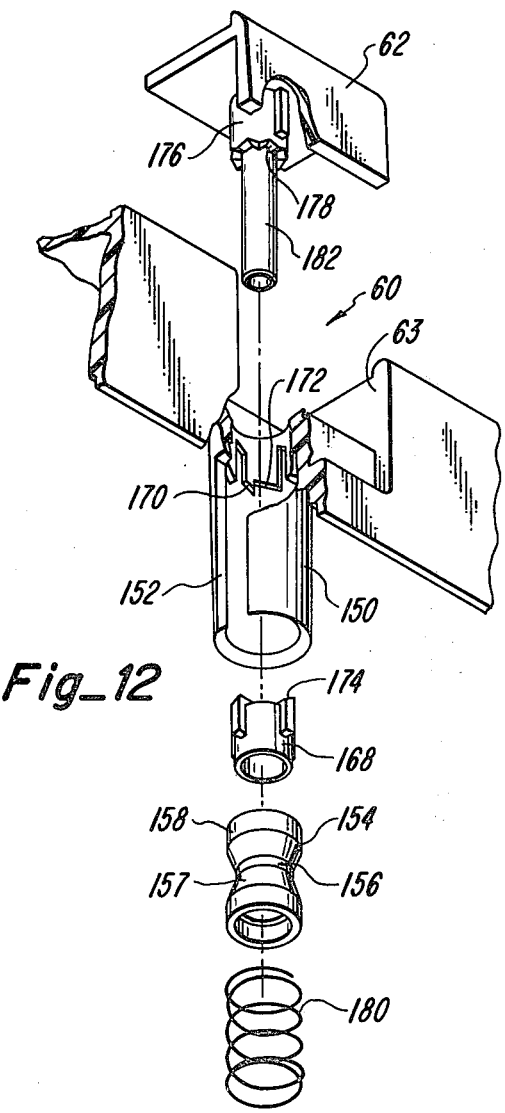
*Fig_12*
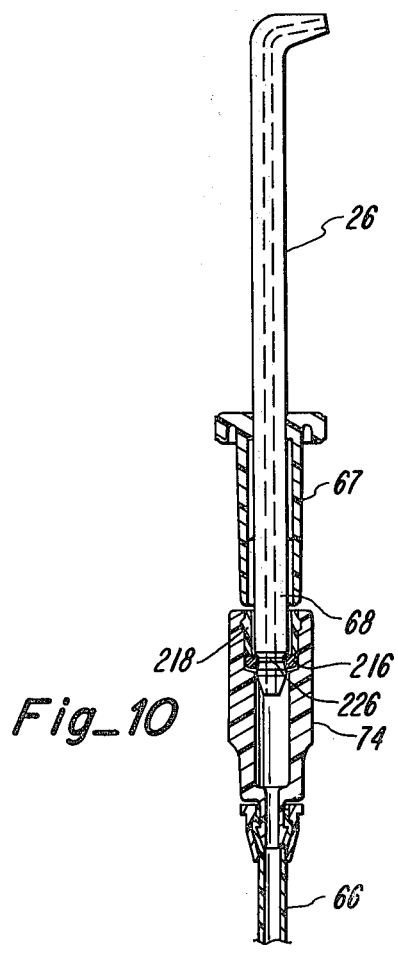
*Fig_10*

ORAL HYGIENE APPLIANCES

The present invention pertains to oral hygiene appliances. It also relates to improvements in switching mechanism, valving assembly, pump structure and mounting arrangements.

Widespread consumer acceptance has been found to exist for oral hygiene devices that provide pulsed jets of water which are directed against the teeth and gums for the purpose of cleaning the teeth and massaging the gums. Methods and apparatus for those purposes are described and claimed in U.S. Pat. Nos. 3,227,158, Re. 27,274, 3,453,969, 3,467,083, 3,425,410 and 4,108,167. All of those patents are assigned to the same assignee as the present application. The commercial embodiments which have included the inventions of those patents have usually involved an attractively styled unit with a removable cover that, when inverted, serves as a reservoir for water supplied to the unit. Within the unit is a motor-driven pump the outlet of which is coupled through a flexible hose to a hand-held nozzle that the user employs to direct pulsating jets against his teeth and gums.

In an effort to achieve durability while at the same time effecting manufacturing economy, attention has been given to the formation of as many components as possible from plastic material. For example, even the pump cylinder block and the cooperating piston as well as the piston rod have successfully been entirely molded and formed from plastic materials.

Although the various embodiments described in the aforementioned patents have all been developed primarily for use in the dental field, the same apparatus also have found usage in other implementations such as wound debridement, the cleaning of the ear canel and other medical applications. In addition, some of the mechanical and electrical improvements involved have been of a nature to lend themselves to use in entirely different environments.

In at least one case, a number of the earlier device developments were implemented in an oral hygiene appliance which was particularly suitable for portable use. That is, it was arranged to have a form factor and compact size that made it more suitable than some of the standard models for packing and storage within a suitcase or the like, so as to be available when traveling. Although advantageous in many respects, that unit was still too bulky for convenient storage for transport in smaller containers such as briefcases, handbags, shaving kits, pouches or coat pockets.

To be described in detail is a specific embodiment of an improved oral hygiene appliance. At the same time, it will be recognized that detailed features of improvement also have application to other forms of oral hygiene appliances as well as to devices other than those useful strictly in that field. Accordingly, it is a general object of the present invention to provide a new and improved oral hygiene appliance as well as features that have beneficial application elsewhere.

Another object of the present invention is to provide a new and improved oral hygiene device which is very compact and yet is fully capable of achieving the desired and appropriate results.

A further object of the present invention is to provide a new and improved switch mechanism for such a device.

Still another object of the present invention is to provide a new and improved pump structure as employed in that kind of apparatus.

A still further object of the present invention is to provide a new and improved mounting arrangement that facilitates the attainment of compactness and yet which permits the device to be conveniently rested in a stable orientation when in position for use on a countertop or the like.

A detailed object of the present invention is to provide a new and improved reservoir valving assembly.

The invention is thus embodied in a device which includes a supply of liquid, a pump for propelling that liquid and means for delivering the propelled liquid to a point of use. A housing defines a cavity and has a surrounding wall closed by opposing end walls, the pump being seated within the cavity. A reservoir, closed at one end and open at the other end, has a shape in conformity with the housing to telescope thereover in covering relationship with the surrounding wall and one of the end walls. Defined in the one end of the reservoir is a valve seat that cooperates with a valve which is normally closed when a supply of the liquid is contained in the reservoir during its removal from the aforesaid covering relationship. A coupling element on the reservoir is in liquid communication with the valve seat, while a coupling member disposed in the surrounding wall of the housing is matable with the coupling element upon placement of the one reservoir end wall adjacent to the surrounding wall of the housing and in a position overlying the coupling member. Disposed in the housing wall is an outlet for communication with the delivering means, and the device includes means connecting the pump between the coupling member and the outlet. Various aspects of the invention are particularly directed to pump structure, the valving and coupling arrangements, the approach to electrical switching and the overall interrelationships among such components.

The features of the present invention which are believed to be patentable are set forth with particularity in the appended claims. The organization and manner of operation of the invention, together with further objects and advantages thereof, may best be understood by reference to the following description taken in connection with the accompanying drawings, in the several figures of which like reference numerals identify like elements, and in which:

FIG. 1 is an isometric view of an oral hygiene appliance with a reservoir disposed in a storage position on a housing;

FIG. 2 is a front elevational view of the appliance with the reservoir and housing in operative positions and with additional components mounted on the housing;

FIG. 3 is a cross-sectional view taken along the line 3—3 in FIG. 2, the additional components having been removed;

FIG. 4 is a cross-sectional view taken along the line 4—4 in FIG. 2;

FIG. 5 is a fragmentary and enlarged cross-sectional view of a fluid coupling assembly shown in FIG. 4;

FIG. 6 is a fragmentary and enlarged cross-sectional view of a pump assembly and coupling shown in FIGS. 2-4;

FIG. 7 is a fragmentary and enlarged cross-sectional view of a motor assembly shown in FIG. 3;

FIG. 8 is a fragmentary and enlarged cross-sectional view of a coupling element in a storage position as shown in FIGS. 2 and 4;

FIG. 9 is an enlarged isometric view of an electrical connection assembly shown in FIG. 3;

FIG. 10 is an enlarged and fragmentary cross-sectional view of coupling components shown in FIGS. 2 and 4 but fitted together in operative position;

FIG. 11 is an enlarged and fragmentary cross-sectional view of an electrical switch and connector assembly shown in FIG. 3; and FIG. 12 is an exploded isometric view of the switch assembly shown in FIG. 11.

An oral hygiene appliance or device 20 includes a housing 22 associated with a reservoir 24 and nozzles 26. In use, reservoir 24 contains a supply of water or other liquid that is supplied to and propelled by a pump 28, located within housing 22, and delivered by a selected one of nozzles 26 to the point of use within a person's mouth for cleaning the teeth and massaging the gums.

Housing 22 is formed by shells 29 and 30 which mate together to define a cavity 32 thus bounded by a surrounding wall 34 and opposing end walls 36 and 38, using FIG. 4 for reference as to "end". Reservoir 24 is closed at one end 40 and open at its other end 42. As shown in FIG. 1, reservoir 24 has a shape which is in conformity with housing 22, so as to telescope thereover in covering relationship with most of surrounding wall 34 and its end wall 36 for storage when the appliance is not in use and for convenience during transport.

Defined in reservoir end 40 is a valve seat 46 that cooperates with a valve 48. The valve is normally closed to the valve seat when reservoir 24 contains water and is removed from its telescopically covering relationship with housing 22. In liquid communication with valve seat 46 on end 40 of reservoir 24 is a coupling 50. Matable with the latter in further liquid communication is a coupling member 52 disposed in surrounding wall 34 of housing 22 upon placement of reservoir end wall 40 adjacent to surrounding wall 34 and in a position to overlie member 52 (FIGS. 4 and 5).

Disposed in end wall 38 of housing 22, for communication with nozzle 26, is an outlet opening 54 that is so located as to be free of any part of reservoir 24 when the latter is placed in its aforementioned covering relationship with respect to the housing. Pump 28 is disposed within cavity 32 and connected between coupling member 52 and outlet opening 54.

It will be observed that surrounding wall 34 is of generally rectangular cross section, so as to have space-opposed generally-planar panels 55 and 56 along longer sides of that cross section. For use, as shown in FIGS. 2 and 4, reservoir 24 is to be placed with its end wall 40 adjacent to the upper panel 55, and the other opposed panel 56 serves as a supporting base for the entire device as when resting on a countertop or the like.

Seated within cavity 32 is an electric motor 58 connected to drive pump 28 and associated with a switch 60 for energizing the motor. Switch 60 includes an operator or button 62 disposed in shell 29 of housing 22 in a location which is free of all portions of reservoir 24 when the latter is placed in position for use as shown in FIGS. 2 and 4. As shown in FIG. 2, button 62 is in its "off" position. When in its "on" position, button 62 is moved downwardly within a recess 63.

To be coupled between outlet opening 54 and one of nozzles 26 is a flexible hose 66. Each nozzle 26 projects through a base 67 formed at its lower end to receive the lower end 68 of the nozzle. Lower end 68 may be seated in one of recesses 69 formed into a portion of the upper panel of shell 29 that is free of reservoir 24 when the latter is situated for use. Thus, the nozzle assemblies may be stored alongside reservoir 24 when the reservoir is positioned in its use orientation.

Projecting inwardly from opening 54 in housing end wall 38, and in this case formed as an integral part of the structure which includes pump 28, is a well 70 that serves as part of connecting means for coupling the pump output into the bottom of well 70. Connected to the end of hose 66 that is to be opposite nozzle 26 is a plug 71 that is insertable removably into well 70 and is hollow so as to transmit liquid from pump 28 into hose 66. An O-ring 72 seals plug 71 within well 70.

Affixed on the other end of hose 66 is a hollow coupling 74 into which lower end 68 is seated during operation (FIG. 10). For temporary storage, on the other hand, coupling 74 may be seated on a post 75 that projects upwardly from a shelf 76 on plug 71 when the latter is inserted into well 70 (FIGS. 2, 4 and 8). A pair of oppositely spaced recesses 77 and 78 (FIG. 3) are defined at corresponding sides of opening 54 and formed to have respective different sizes. Correspondingly formed lugs 79 and 80 (FIG. 4) project laterally from plug 71 and serve to permit insertion of plug 71 within opening 54 in only one appropriate rotational position. Recesses 77 and 78 cooperate with space-opposed detents 81. The housing wall is sufficiently flexible to provide a spring action so that lugs 79 and 80 are cammed over detents 81 and into a locked position upon insertion of plug 71 into place.

Also seated within cavity 32 is a battery 82 for energizing motor 58 and removably insertable through an opening 84 defined in a side wall portion 86 of surrounding wall 34. Opening 84 is closed by a cover plug 88.

Button 62 normally rests in a position which is flush with panel 55 of surrounding wall 34 and end wall 38 within which it is disposed, and the button is located to be free of reservoir 24 when either in its storage position as shown in FIG. 1 or in its use position as shown in FIGS. 2 and 4. In the orientation of FIG. 1, a portion on button 62 and outlet opening 54 in end wall 38 are concealed from view on the underside of the unit. On the other hand, coupling member 52 is disposed in panel 55 of surrounding wall 34 to be concealed from external view when reservoir 24 is inverted as in FIG. 1 to face its closed end 40 upwardly and is telescoped into covering relationship with housing 22 as end wall 38 rests on a substrate.

Pump 28 includes a generally T-shaped hollow body 90, and a chamber 92 is defined in its leg 94 (FIG. 6). Disposed for reciprocation within chamber 92 is a piston 96 coupled by a rod 98 eccentrically to a face gear 100 driven in rotation by a spur gear 102 on the output shaft of motor 58 (FIG. 7).

One arm 106 of pump body 90 is disposed at and effectively coupled to outlet 54 by an intergral extension which defines well 70. Beneath well 70 in arm 106 is a cross-wall in which is defined an exit orifice 107. The other arm 108 of pump body 90 is coupled to member 52. A check valve 110, slidable within a valve guide 112, is disposed within arm 108 and poled by a compression spring 114 to pass liquid only from coupling member 52 and on into chamber 92 (FIG. 6). Valve guide 112 also forms a fluid seal.

Coupling element 50 includes a snout 116 that projects outwardly from end 40 of reservoir 24 and is aligned for liquid communication with valve seat 46. Coupling member 52 includes a well 118 defined in panel 55 of surrounding wall 34 and matable in liquid communication with snout 116 upon placement of end wall 40 against panel 55 of housing 22 and in a position to overlie well 118. An opening 122 is defined in the bottom of well 118. Coupled at one end to pump 28 and forming an integral lateral projection from an end cap 123 on arm 108 of pump body 90 is a tube 124. Tube 124 is disposed to project its free end through opening 122.

A seal 126 disposed within opening 122 includes a sleeve 128 seated between opening 122 and tube 124. Seal 126 also includes a skirt 130 that is flared away from sleeve 128 and into engagement with the interior wall of snout 116 when reservoir 24 is mounted as shown in FIGS. 4 and 5. Tube 124 is tapered in wall thickness as shown to cause sleeve 128 to flare outwardly on assembly and thereby become locked in position.

Valve 48 includes a tube-shaped operator portion 134 that faces the free end of tube 124 which serves as an abutment. That free end is disposed in a position to engage operator 134 and open valve 48 when end wall 40 of reservoir 24 is placed into the use position. Operator 134 is a coupler which moves inside valve seat 46. Included as a part thereof are a plurality of circumferentially-spaced resilient fingers 136 each of which has a laterally-facing lip 138 that is insertable through the inside of valve seat 46 to snap into place adjacent to the surface of reservoir end wall 40 opposite seat 46. Valve 48 is thereby captivated between open and closed positions.

Defined on the interior of end wall 40 of reservoir 24 is a recess 142 that surrounds valve seat 46. Included on valve 48 are a plurality of circumferential flutes 144 that face the internal wall of recess 142 and define therewith a strainer when valve 48 is open with respect to valve seat 46. That is, valve 48 is formed to combine in but one part the combination of both a strainer element and a valve element. Valve 48 is lifted only enough to open a fluid path between fingers 136, while yet creating a restriction against the passage into the pump body of any large particles of foreign matter.

Button 62 is depressably mounted in its exposed position on housing 22. Defined within the housing is a barrel 150 beneath button 62 (FIGS. 11 and 12). An opening 152 is defined longitudinally through the wall of barrel 150. Slidable longitudinally within the barrel is a spool 154 that has a circumferential central V-shaped groove 156 to present a first surface 157 which faces opening 152 and is axially spaced from a second surface 158 on a remaining portion of the external wall of spool 154. That is, the bottom of groove 156 is spaced a different distance from opening 152 than is surface 158.

Spool 154 is movable axially within barrel 150 between first and second positions in alternate directions upon successive depressions of button 62. A resilient conductive finger 160 projects through opening 152 and against the exterior wall of spool 154. Movement of the spool between its first and second positions aligns respective different ones of groove 156 and surface 158 in engagement with finger 160, so as correspondingly to change locations of a contact portion 162 on finger 160. A conductive contact element 164 is disposed in the path of contact portion 162 and is engageable and disengageable with the latter upon its change between such locations. Contact portion 162 and contact element 164 are connected in circuit with motor 58 and battery 82.

Moving spool 154 between its two different positions is a rotatable cam cylinder 168 disposed within barrel 150 adjacent to spool 154. A plurality of cam operators 170 and stops 172 defined on and circumferentially spaced alternately around the inner wall of barrel 150 cooperate with cam surfaces 174 correspondingly circumferentially-spaced around the circumference of cylinder 168. Projecting inwardly from button 62 is a driver 176 on which are defined cam elements 178 that also cooperate with cam surfaces 174. A compression spring 180, disposed on the end of spool 154 opposite cylinder 168, urges spool 154, cylinder 168 and driver 176 together. Projecting integrally downward also from button 62, and having a diameter less than that of driver 176, is a spindle 182 upon which cylinder 168 and spool 154 are longitudinally slidable. Barrel 150 projects above the bottom of recess 63 as a boss 184, serving to prevent water that leaks around the edges of button 62 from entering the interior of the housing. In this case, a retaining screw 185 serves to secure the internal switch parts into operative relationship and to hold button 62 in place (FIG. 11).

The resulting switch combination operates in a manner similar in principle to that involved in connection with the push-push operation of one mechanism particularly employed in ball point pens for moving the reservoir and writing point within a barrel. Each depression of button 62 causes cylinder 168 to be rotated one step by driver 176 as a result of which the ends of cams 174 alternately are held downwardly against stops 172 and allowed to pass upwardly between cam operators 170. That alternate positioning serves correspondingly to cause the alternate opening and closing of contact member 162 with contact element 164. A principal difference from the mentioned mechanism employed in a ball-point pen resides in the separation of cylinder 168 from spool 154. Consequently, cylinder 168 is free to rotate even though spool 154 is under a side loading imposed by contact finger 160.

A plurality of integrally-formed webs 190 are disposed within each of shells 29 and 30 and arranged as shown in FIGS. 3 and 4 to define a plurality of compartments. Also projecting toward one another are a plurality of mating posts 192 that mate as between the respective shells so as to fasten them together upon the insertion of screws (not shown). Different ones of the wells as illustrated define appropriate recesses as at 194 so as to snugly captivate and seat pump body 90. Motor 58 is similarly seated and supported in a recess 195. Moreover, lugs on the frame of motor 58 are trapped by the webs that define recess 195. This constrains motor movement as against the forces resulting from the eccentric drive system for the pump unit. A projection 196 serves to mount contact element 164.

Also defined by the arrangement of webs 190 and as illustrated is a compartment for battery 82. Mounted within housing 22 and having a receptacle 198 exposed to the exterior through wall portion 86 is a plug 199 for connection to a separate battery charger. For contact against one end of battery 82 is a connector 200 (FIGS. 3 and 9). Another connector 202 is correspondingly disposed so as to have one end portion engageable with the other end of battery 82 and another end portion engageable with receptacle 198. Conductive finger 160 is connected to and projects away from connector 200 so as to locate its contact member 162 alongside contact element 164. Suitable interconnecting leads as shown in FIGS. 3, 7 and 11 are included so as to complete the circuitry between battery 82, motor 58, contact element 164, charger receptable 198 and connectors 200 and 202.

In this case formed on end wall 36 of housing 22 is a protrusion 210 in which is defined a somewhat V-shaped recess 212. Recess 212 may be used to mount the entire unit, when desired, upon a matingly shaped bracket (not shown) that may be secured to a wall for more permanent installation of the appliance. For transport, the entire assemblage preferably is contained within a case provided with a plurality of recesses into which the different detachable components are seated.

Referring back to FIGS. 8 and 10, it will be noted that lower end 68 of nozzle 26 is secured with a snap fit in coupling 74 by a floating O-ring 216. The latter is captivated in the bore of coupling 74 by a retaining sleeve 218 that defines a recess. The snap fit is effected by a groove 226 formed around the terminal end portion of lower end 68.

A compact and readily portable oral hygiene appliance results from the construction and assembly described. The manner in which the different components and subcomponents are formed permits quick and easy assembly or parts replacement. Except for the battery, motor and conductive elements, all of the various parts may be economically molded from a plastic material. Although a water pressure control is not specifically included in the illustrated embodiment, adjustment with respect to that function is still available for the user by the provision of two or more different ones of interchangeable nozzles 26 respectively having different sizes of outlet orifices.

It may also be observed that different ones of the subcomponents described have the capability of separate utility in other appliances and like devices. For example, pump 28 together with motor 58 constitute a simple and yet quite effective liquid pumping unit easily adaptable to other forms of oral hygiene appliances and various devices of different kinds. The described switching mechanism has independent utility in other devices and environments.

While a particular embodiment of the invention has been shown and described, it will be obvious to those skilled in the art that changes and modifications may be made without departing from the invention in its broader aspects. Therefore, the aim in the appended claims is to cover all such changes and modifications as fall within the true spirit and scope that which is patentable.

We claim:

1. In a device which includes a supply of liquid, a pump for propelling said liquid, and means for delivering the propelled liquid to a point of use, the improvement comprising:
    a housing defining a cavity having a surrounding wall closed by opposing end walls and with said pump being seated within said cavity;
    a reservoir, closed at one end and open at the other end, having a shape in conformity with said housing to telescope thereover in covering relationship with said surrounding wall and one of said end walls;
    a valve seat defined in said one end of said reservoir;
    a valve normally closed to said valve seat with said supply of liquid contained in said reservoir during removal thereof from said covering relationship;
    a coupling element on said one end of said reservoir and in liquid communication with said valve seat;
    a coupling member disposed in said surrounding wall and matable in liquid communication with said coupling element upon placement of said one end adjacent to said surrounding wall and in a position overlying said coupling member;
    an outlet disposed in a wall of said housing for fluid communication with said delivering means and in a location free of said one end during said placement;
    and means connecting said pump between said coupling member and said outlet.

2. A device as defined in claim 1 in which said surrounding wall is of generally rectangular cross section having space-opposed generally planar panels along longer sides of said cross section, and in which said placement of said one end is adjacent to one of said panels with the other of said panels serving as a support base for said device.

3. A device as defined in claim 1 in which said outlet is disposed in one of said end walls of said housing.

4. A device as defined in claim 1 which includes an electric motor seated in said cavity for driving said pump and a switch for energizing said motor, and in which said switch includes an operator disposed in a wall portion of said housing in a location free of said one end during said placement.

5. A device as defined in claim 1 in which said delivering means includes a flexible hose coupled at one end to said outlet and with a nozzle removably coupled to the other end of said hose, and which includes means, in a continuation of the portion of said surrounding wall to which said one end is adjacent during said placement but yet then free of said one end, for storing said nozzle alongside said reservoir as so placed and when said nozzle is uncoupled from said hose.

6. A device as defined in claim 1 in which said delivering means includes a flexible hose coupled at one end to a nozzle, which includes a well depending inwardly from a wall of said housing, in which said connecting means couples the output of said pump into the bottom of said well, in which a plug is connected to the other end of said hose and is sealingly insertable removably into said well to transmit liquid from said pump to said hose.

7. A device as defined in claim 1 which includes an electric motor seated in said cavity for driving said pump and a battery for energizing said motor, means in said cavity defining a seat for said battery and means defining an opening in a wall of said housing and through which said battery is insertable.

8. A device as defined in claim 1 which includes an electric motor seated in said cavity for driving said pump and a switch for energizing said motor with said switch having an operator disposed in a wall portion of said housing and normally resting in a position flush with said wall portion, said coupling member and said outlet being disposed in respective wall portions of said housing concealed from external view when said reservoir is inverted to dispose said one end upwardly and telescoped into said covering relationship with said housing resting on a substrate.

9. A device as defined in claim 1 in which said coupling member and said outlet are disposed in respective wall portions of said housing concealed from external view when said reservoir is inverted to dispose said one end upwardly and telescoped into said covering relationship with said housing resting on a substrate.

10. In a device which includes a supply of liquid, a pump for propelling said liquid, and means for delivering the propelled liquid to a point of use, the improvement comprising:

a housing defining a cavity having a surrounding wall closed by opposing end walls and with said pump being seated within said cavity;
a reservoir, closed at one end and open at the other end, having a shape in conformity with said housing to telescope thereover in covering relationship with said surrounding wall and one of said end walls;
a valve seat defined in said one end of said reservoir;
a valve normally closed to said valve seat with said supply of liquid contained in said reservoir during removal thereof from said covering relationship;
a coupling element on said one end of said reservoir and in liquid communication with said valve seat;
a coupling member disposed in said surrounding wall and matable in liquid communication with said coupling element upon placement of said one end adjacent to said surrounding wall and in a position overlying said coupling member;
an outlet disposed in a wall of said housing for fluid communication with said delivering means and in a location free of said one end during said placement;
means connecting said pump between coupling member and said outlet;
an electric motor seated in said cavity for driving said pump;
said pump having a generally T-shaped hollow body with a chamber defined in its leg;
a piston disposed for reciprocation in said chamber;
means coupled to said motor for reciprocating said piston;
means for coupling the end of one arm of said body to said outlet;
and means for coupling the end of the other arm of said body to said coupling member.

11. In a device which includes a supply of liquid, a pump for propelling said liquid, and means for delivering the propelled liquid to a point of use, the improvement comprising:

a housing defining a cavity within which said pump is seated;
means defining an outlet in said housing;
means defining an inlet coupling member in said housing;
an electric motor seated in said cavity for driving said pump;
said pump having a generally T-shaped hollow body with a chamber defined in its leg;
a piston disposed for reciprocation in said chamber;
means coupled to said motor for reciprocating said piston;
means for coupling the end of one arm of said body to said outlet;
and means for coupling the end of the other arm of said body to said coupling member.

12. A device as defined in claim 10 or 11 which includes a check valve disposed in said other arm and poled to pass liquid only from said coupling member to said chamber.

13. In a device which includes a supply of liquid, a pump for propelling said liquid, and means for delivering the propelled liquid to a point of use, the improvement comprising:

a housing defining a cavity having a surrounding wall closed by opposing end walls and with said pump being seated within said cavity;
a reservoir, closed at one end and open at the other end, having a shape in conformity with said housing to telescope thereover in covering relationship with said surrounding wall and one of said end walls;
a valve seat defined in said one end of said reservoir;
a valve normally closed to said valve seat with said supply of liquid contained in said reservoir during removal thereof from said covering relationship;
a coupling element on said one end of said reservoir and in liquid communication with said valve seat;
a coupling member disposed in said surrounding wall and matable in liquid communication with said coupling element upon placement of said one end adjacent to said surrounding wall and in a position overlying said coupling member;
an outlet disposed in a wall of said housing for fluid communication with said delivering means and in a location free of said one end during said placement;
means connecting said pump between coupling member and said outlet;
said coupling element including a snout projecting outwardly from said one end of said reservoir;
said coupling member including a well defined in said surrounding wall;
means defining an opening in the bottom of said well;
a tube coupled at one end of said pump and disposed to project its other end through said opening;
and means for sealing said other end of said tube within said opening and to said snout.

14. In a device which includes a supply of liquid, a pump for propelling said liquid, and means for delivering the propelled liquid to a point of use, the improvement comprising:

a housing defining a cavity within which said pump is seated;
a reservoir, closed at one end and open at the other end, having a shape in conformity with said housing to telescope thereover in a covering relationship;
a valve seat defined in said one end of said reservoir;
a valve normally closed to said valve seat with said supply of liquid contained in said reservoir and said reservoir removed from said covering relationship;
a coupling element including a snout projecting outwardly from said one end of said reservoir and in liquid communication with said valve seat;
a coupling member including a well defined in said housing and matable in liquid communication with said coupling element upon placement of said one end adjacent to said housing and in a position overlying said coupling member;
an outlet disposed in a wall of said housing for fluid communication with said delivering means;
means connecting said pump between said coupling member and said outlet;
means defining an opening in the bottom of said well;
a tube coupled at one end to said pump and disposed to project its other end through said opening;
and means for sealing said other end of said tube within said opening and to said snout.

15. A device as defined in claim 13 or 14 in which said sealing means includes a sleeve seated between said opening and said tube and a skirt flared away from one sleeve end and into engagement with the interior wall of said snout.

16. A device as defined in claim 13 or 14 in which said valve includes an operator portion facing the free end of said tube, and in which said free end is disposed in a position to engage said operator portion and open said valve upon said placement of said one end wall.

17. A device as defined in claim 16 in which said operator portion includes a tube-shaped coupler movable inside said valve seat and defining a circumferential lateral lip engageable with a surface opposite said valve seat to captivate said valve between open and closed positions.

18. A device as defined in claim 17 in which said coupler is composed of a plurality of circumferentially-spaced resilient fingers each having a laterally-facing lip portion insertable through the inside of said valve seat to snap into place adjacent to said surface.

19. In a device which includes a supply of liquid, a pump for propelling said liquid, and means for delivering the propelled liquid to a point of use, the improvement comprising:
a housing defining a cavity having a surrounding wall closed by opposing end walls and with said pump being seated within said cavity;
a reservoir, closed at one end and open at the other end, having a shape in conformity with said housing to telescope thereover in covering relationship with said surrounding wall and one of said end walls;
a valve seat defined in said one end of said reservoir;
a valve normally closed to said valve seat with said supply of liquid contained in said reservoir during removal thereof from said covering relationship;
a coupling element on said one end of said reservoir and in liquid communication with said valve seat;
a coupling member disposed in said surrounding wall and matable in liquid communication with said coupling element upon placement of said one adjacent to said surrounding wall and in a position overlying said coupling member;
an outlet disposed in a wall of said housing for fluid communication with said delivering means and in a location free of said one end during said placement;
means connecting said pump between coupling member and said outlet;
means defining a recess in said one end of said reservoir and surrounding said valve seat, said valve including a plurality of circumferential flutes facing the internal wall of said recess and defining therewith a strainer when said valve is opened with respect to said valve seat.

20. In a device which includes a supply of liquid, a pump for propelling said liquid, and means for delivering the propelled liquid to a point of use, the improvement comprising:
a housing defining a cavity within which said pump is seated;
a reservoir, closed at one end and open at the other end, having a shape in conformity with said housing to telescope thereover in a covering relationship;
a valve seat defined in said one end of said reservoir;
a valve normally closed to said valve seat with said supply of liquid contained in said reservoir during removal thereof from said covering relationship;
a coupling element on said one end of said reservoir and in liquid communication with said valve seat;
a coupling member disposed in said housing and matable in liquid communication with said coupling element upon placement of said one end adjacent to said housing and in a position overlying said coupling member;
an outlet disposed in a wall of said housing for fluid communication with said delivering means;
means connecting said pump between said coupling member and said outlet;
means defining a recess in said one end of said reservoir and surrounding said valve seat;
and means defining a plurality of circumferential flutes on said valve and facing the internal wall of said recess to define therewith a strainer when said valve is opened with respect to said valve seat.

21. A device as defined in claim 1 in which said valve includes an operator portion movable inside said valve seat and defining a circumferential lateral lip engageable with a surface opposite said valve seat to captivate said valve between open and closed positions.

22. In a device which includes a supply of liquid, a pump for propelling said liquid, and means for delivering the propelled liquid to a point of use, the improvement comprising:
a housing defining a cavity within which said pump is seated;
a reservoir, closed at one end and open at the other end, having a shape in conformity with said housing to telescope thereover in a covering relationship;
a valve seat defined in said one end of said reservoir;
a valve normally closed to said valve seat with said supply of liquid contained in said reservoir during removal thereof from said covering relationship;
a coupling element on said one end of said reservoir and in liquid communication with said valve seat;
a coupling member disposed in said housing and matable in liquid communication with said coupling element upon placement of said one end adjacent to said housing and in a position overlying said coupling member;
an operator portion on said valve and movable inside said valve seat;
and a circumferential lateral lip on said operator portion and engageable with a surface opposite said valve seat to captivate said valve between open and closed positions.

23. A device as defined in claim 21 or 22 in which said operator portion is composed of a plurality of circumferentially-spaced resilient fingers each having a laterally-facing lip portion insertable through the inside of said valve seat to snap into place adjacent to said surface.

24. A device as defined in claim 21 or 22 in which said coupling member includes means defining an abutment disposed in a position to engage said operator portion and open said valve upon said placement of said one end.

25. In a device which includes a supply of liquid, a pump for propelling said liquid, and means for delivering the propelled liquid to a point of use, the improvement comprising:
a housing defining a cavity having a surrounding wall closed by opposing end walls and with said pump being seated within said cavity;
a reservoir, closed at one end and open at the other end, having a shape in conformity with said housing to telescope thereover in covering relationship with said surrounding wall and one of said end walls;

a valve seat defined in said one end of said reservoir;

a valve normally closed to said valve seat with said supply of liquid contained in said reservoir during removal thereof from said covering relationship;

a coupling element on said one end of said reservoir and in liquid communication with said valve seat;

a coupling member disposed in said surrounding wall and matable in liquid communication with said coupling element upon placement of said one end adjacent to said surrounding wall and in a position overlying said coupling member;

an outlet disposed in a wall of said housing for fluid communication with said delivering means and in a location free of said one end during said placement;

means connecting said pump between said coupling member and said outlet;

an electric motor seated in said cavity for driving said pump and a switch for energizing said motor with said switch further including;

a button depressably mounted in an exposed position in a wall portion of said housing;

a barrel disposed in said housing beneath said button with an opening being defined through the wall of said barrel;

a spool slidable longitudinally within said barrel and having a pair of axially-spaced external wall surfaces facing said opening individually at respective different distances therefrom;

means coupled between said button and said spool for moving said spool axially between first and second positions in alternate directions upon successive depressions of said button;

a resilient conductive finger projecting through said opening and against said spool, movement of said spool between said first and second positions aligning respective different ones of said surfaces in engagement with said finger and correspondingly changing locations of a contact portion on said finger;

a conductive contact element disposed in the path of said contact portion and engageable and disengageable therewith upon change between said locations;

and means for connecting said contact portion and said contact element in circuit with said motor.

26. In an oral hygiene appliance which includes a liquid reservoir, a pump for propelling said liquid, and means for delivering the propelled liquid from said reservoir to a point of use, the improvement comprising:

a housing for said pump shaped with respect to said reservoir to accept the latter telescopingly in at least partially enclosing relationship during storage of said appliance;

means defined in said reservoir and said housing for enabling the supply of said liquid, contained in said reservoir, into said housing and to said pump, only upon mutual re-orientation of said housing and said reservoir to present a mutually-reversed aspect of said reservoir in coupling and orthogonally different relationship with said housing.

27. An oral hygiene appliance as defined in claim 26 in which said reservoir covers one side of said housing during said storage and is inverted and then placed against another side of said housing, orthogonally related to said one side, to effect said coupling relationship.

28. An oral hygiene appliance as defined in claim 26 in which said housing includes an outlet port, and in which said outlet port remains uncovered by said reservoir in either orientation thereof.

29. An oral hygiene appliance as defined in claim 26 in which said reservoir, when so telescoped, only partially covers said housing but conceals from view all unaesthetic portions of said housing not concealed by then disposition of the housing.

30. In an oral hygiene appliance which includes a liquid reservoir, a pump for propelling pulsed jets of said liquid, and means for delivering the propelled liquid from said reservoir to the teeth and gums of the user, the improvement comprising the combination of:

a coupling communicating with said pump for outletting pulses of said liquid;

a plurality of nozzles, each capable of being grasped to direct said liquid against said teeth and gums, individually engageable with said coupling for delivering said liquid therefrom;

and said nozzles individually having respectively different outlet orifice sizes to enable selection of outletted pressure of said liquid.

* * * * *